(12) United States Patent
Miyake et al.

(10) Patent No.: US 9,814,236 B2
(45) Date of Patent: *Nov. 14, 2017

(54) AGRICULTURAL OR HORTICULTURAL CHEMICAL, METHOD OF CONTROLLING PLANT DISEASES, AND PRODUCT FOR CONTROLLING PLANT DISEASES

(71) Applicant: Kureha Corporation, Tokyo (JP)

(72) Inventors: Taiji Miyake, Tokyo (JP); Nobuyuki Araki, Tokyo (JP)

(73) Assignee: Kureha Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/035,514

(22) PCT Filed: Oct. 8, 2014

(86) PCT No.: PCT/JP2014/076905
§ 371 (c)(1),
(2) Date: May 10, 2016

(87) PCT Pub. No.: WO2015/083436
PCT Pub. Date: Jun. 11, 2015

(65) Prior Publication Data
US 2016/0270398 A1 Sep. 22, 2016

(30) Foreign Application Priority Data
Dec. 5, 2013 (JP) .................... 2013-252539

(51) Int. Cl.
*A61K 31/41* (2006.01)
*A01N 43/653* (2006.01)
*A01N 43/50* (2006.01)
*A01N 37/34* (2006.01)
*A01N 43/40* (2006.01)
*A01N 43/56* (2006.01)
*A01N 47/08* (2006.01)

(52) U.S. Cl.
CPC ........... *A01N 43/653* (2013.01); *A01N 37/34* (2013.01); *A01N 43/40* (2013.01); *A01N 43/50* (2013.01); *A01N 43/56* (2013.01); *A01N 47/08* (2013.01)

(58) Field of Classification Search
USPC ........................................ 514/355, 406, 407
See application file for complete search history.

(56) References Cited

U.S. PATENT DOCUMENTS

| | | |
|---|---|---|
| 4,503,063 A | 3/1985 | Richardson et al. |
| 4,547,214 A | 10/1985 | Crowley et al. |
| 4,904,682 A | 2/1990 | Kramer et al. |
| 4,938,792 A | 7/1990 | Kumazawa et al. |
| 5,028,254 A | 7/1991 | Kumazawa et al. |
| 5,047,548 A | 9/1991 | Richardson et al. |
| 5,159,118 A | 10/1992 | Kumazawa et al. |
| 5,239,089 A | 8/1993 | Kumazawa et al. |
| 5,256,683 A | 10/1993 | Hutt et al. |
| 5,292,764 A | 3/1994 | Arahira et al. |
| 5,380,743 A | 1/1995 | Hutt et al. |
| 5,414,105 A | 5/1995 | Kumazawa et al. |
| 5,639,918 A | 6/1997 | Hutt et al. |
| 9,035,069 B2 * | 5/2015 | Araki .................. A01N 43/653 548/262.2 |
| 9,278,941 B2 * | 3/2016 | Araki ..................... A01N 43/50 |
| 2011/0124877 A1 | 5/2011 | Ito et al. |
| 2013/0143940 A1 | 6/2013 | Long et al. |

(Continued)

FOREIGN PATENT DOCUMENTS

| | | |
|---|---|---|
| CN | 1030232 A | 1/1989 |
| CN | 1044814 A | 8/1990 |

(Continued)

OTHER PUBLICATIONS

European Search Report of EP Application No. 14868148.9 issued Oct. 26, 2016, 6 pages.
Office Action for Ukrainian Patent Application No. a201605022, issued Nov. 7, 2016, 5 pages (w/ English translation).
International Preliminary Report on Patentability for PCT/JP2014/076905, mailed on Jun. 16, 2016, 10 pages.
International Search Report of PCT/JP2014/076905 with mailing date of Jan. 6, 2015.
Office Action for Australian Patent Application No. 2014358488, issued on Sep. 7, 2016, 6 pages.
Office Action for CN Application No. 201510259647.0, Nov. 21, 2016.

(Continued)

*Primary Examiner* — Pancham Bakshi
(74) *Attorney, Agent, or Firm* — Abel Law Group, LLP

(57) ABSTRACT

An agricultural or horticultural chemical according to the present invention is an agricultural or horticultural chemical containing a plurality of active ingredients, the agricultural or horticultural chemical comprises, as one of the active ingredients, an azole derivative represented by general formula (I) below, and can be used as a plant disease controlling agent that can reduce the content of an active ingredient,

[Formula 1]

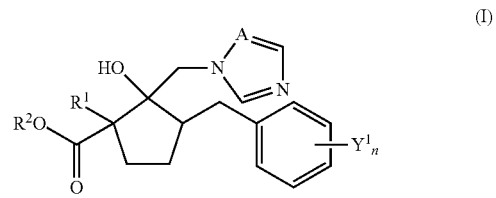

(I)

(In the general formula, $R^1$ represents an alkyl group having from 1 to 6 carbons, $R^2$ represents a hydrogen atom, an alkyl group having from 1 to 3 carbons, an alkenyl group or an alkynyl group having from 2 to 3 carbons, A represents a nitrogen atom or a methine group, $Y^1$ represents a halogen atom, and n represents either 0 or 1).

4 Claims, No Drawings

(56) References Cited

U.S. PATENT DOCUMENTS

| | | | |
|---|---|---|---|
| 2014/0039027 A1* | 2/2014 | Gortz | A01N 43/56 514/406 |
| 2014/0179517 A1 | 6/2014 | Araki et al. | |
| 2014/0315967 A1 | 10/2014 | Araki et al. | |

FOREIGN PATENT DOCUMENTS

| | | | |
|---|---|---|---|
| CN | 103562187 A | 2/2014 | |
| DE | 3902031 A1 | 7/1990 | |
| DE | 4320498 A1 | 12/1994 | |
| EP | 0046633 A1 | 3/1982 | |
| EP | 0086917 A1 | 8/1983 | |
| EP | 0267778 A2 | 5/1988 | |
| EP | 0106515 A2 | 12/1988 | |
| EP | 0313983 A2 | 5/1989 | |
| EP | 0329397 A1 | 8/1989 | |
| EP | 0341954 A1 | 11/1989 | |
| EP | 0488348 A1 | 6/1992 | |
| EP | 951831 | 10/1999 | |
| EP | 2757097 A1 | 7/2014 | |
| EP | 2784067 A1 | 10/2014 | |
| IL | 85428 A | 12/1992 | |
| JP | 58-134079 A | 8/1983 | |
| JP | 59-82376 A | 5/1984 | |
| JP | H01-093574 A | 4/1989 | |
| JP | 1-149776 A | 6/1989 | |
| JP | H01-186871 A | 7/1989 | |
| JP | 1-301664 A | 12/1989 | |
| JP | 2-42003 A | 2/1990 | |
| JP | 4-202190 A | 7/1992 | |
| JP | 5-271197 A | 10/1993 | |
| WO | 2009/088070 A1 | 7/2009 | |
| WO | 2010/023862 A1 | 3/2010 | |
| WO | 2010/074021 A1 | 7/2010 | |
| WO | 2011/070771 A1 | 6/2011 | |
| WO | WO2012169516 A1 | 12/2012 | |
| WO | WO2013077265 A1 | 5/2013 | |

OTHER PUBLICATIONS

Office Action for U.S. Appl. No. 14/359,449, Sep. 8, 2015.
Office Action for EA Application No. 201690801, Nov. 17, 2016.
European Search Report for EP Application No. 14867038.3, Aug. 5, 2016.
International preliminary report on patentability of PCT/JP2014/076906, Jun. 16, 2016.
International Search Report, issued in PCT/JP2014/076906, dated Jan. 6, 2015.
Office Action for AU Application No. 2014358489, Sep. 7, 2016.
International Search Report of PCT/JP2012/079778 dated Dec. 11, 2012.
International preliminary report on patentability of PCT/JP2012/079778, Jun. 19, 2014.
Office Action for EP Application No. 12851782.8, Feb. 4, 2016.
Office Action for CN Application No. 201280056290.0, Jan. 19, 2016.
Office Action of JP application No. 2013-545903 dated Nov. 17, 2015.
International Search Report, issued in PCT/JP2012/064534, dated Jul. 31, 2012.
Extended European Search Report for European Application No, 12797440.0 dated Nov. 19, 2014.
Office Action for CN Application No. 201280056290.0, Jul. 16, 2015.
European Search Report for EP 12851782, Jun. 17, 2015.
Office Action for CN Application No. 201280056290.0, Jan. 23, 2015.
Office Action for U.S. Appl. No. 15/037,534, Nov. 15, 2016.
Notice of acceptance for Australian Application No., 2014358489 dated Jan. 12, 2017.
Office Action for U.S. Appl. No. 15/037,534, Aug. 29, 2016.
Office Action for Eurasia Patent Application No. 201690737, issued Jan. 23, 2017 6 pages (w/ English translation).
Office Action for Ukrainian Patent Application No. a201605022, issued Jan. 10, 2017 2 pages (w/ English translation).
Office Action with regard to European Patent Application No. 14868148.9 dated Jul. 25, 2017.
Office Action with regard to Eurasian Patent Application No. 201690801, dated May 31, 2017 (with English language translation).
Office Action with regard to Canadian application No. 2,930,093, dated Apr. 28, 2017, 8 pgs.
Office Action with regard to Canadian application No. 2,931,346, dated Apr. 28, 2017, 7 pgs.
Office Action with regard to Chinese application No. 201510259647, dated May 2, 2017, 8 pgs.
Office Action with regard to Ukranian application No. a2016 05354, dated Apr. 26, 2017, 8 pgs.

* cited by examiner

AGRICULTURAL OR HORTICULTURAL CHEMICAL, METHOD OF CONTROLLING PLANT DISEASES, AND PRODUCT FOR CONTROLLING PLANT DISEASES

TECHNICAL FIELD

The present invention relates to an agricultural or horticultural chemical, a method of controlling plant diseases, and a product for controlling plant diseases. In particular, the present invention relates to an agricultural or horticultural chemical containing at least one type of azole-based compound as an active ingredient, a method of controlling plant diseases using the same, and a product for controlling plant diseases containing the azole-based compound.

BACKGROUND ART

Certain types of 2-substituted-5-benzyl-1-azolyl methyl cyclopentanol derivatives have been known to exhibit fungicidal activity (e.g. refer to Patent Documents 1 to 3).

CITATION LIST

Patent Literature

Patent Document 1: Japanese Unexamined Patent Application Publication No. H01-93574A (published on Apr. 12, 1989)

Patent Document 2: Japanese Unexamined Patent Application Publication No. H01-186871A (published on Jul. 26, 1989)

Patent Document 3: WO/2012/169516 (published on Dec. 13, 2012)

SUMMARY OF INVENTION

Technical Problem

To-date, agricultural and horticultural chemicals having low toxicity toward human and animals and excellent safety in handling, and exhibiting a high controlling effect against a wide variety of plant diseases have been demanded.

Disease control by agricultural and horticultural chemicals has also raised problems such as the effect on non-target organisms, the effect on the environment, and the emergence of chemical-resistant fungi. For that reason, to reduce toxicity in non-target organisms, to reduce environmental load, and to suppress the emergence of chemical-resistant fungi, an agricultural or horticultural chemical that can exhibit a strong controlling effect with a reduced dispersion quantity has been desired.

The present invention has been made in the light of the above problems. An object of the present invention is to provide an agricultural or horticultural chemical exhibiting an excellent controlling effect and requiring a smaller amount of dispersion to obtain the same degree of effect as that of conventional chemicals.

Solution to Problem

A first aspect of an agricultural or horticultural chemical according to the present invention is an agricultural or horticultural chemical containing a plurality of active ingredients, the agricultural or horticultural chemical comprising: as one of the active ingredients, an azole derivative represented by general formula (I) below; and, as another one of the active ingredients, a compound having a succinate dehydrogenase inhibitory capacity.

[Formula 1]

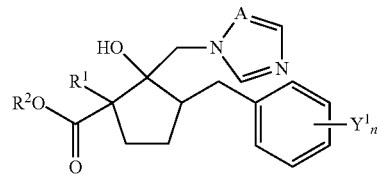

(I)

Additionally, in general formula (I), $R^1$ represents an alkyl group having from 1 to 6 carbons, $R^2$ represents a hydrogen atom, an alkyl group having from 1 to 3 carbons, an alkenyl group having from 2 to 3 carbons or an alkynyl group having from 2 to 3 carbons, A represents a nitrogen atom or a methine group, $Y^1$ represents a halogen atom, and n represents either 0 or 1.

A second aspect of an agricultural or horticultural chemical according to the present invention is an agricultural or horticultural chemical containing a plurality of active ingredients, the agricultural or horticultural chemical comprising: as one of the active ingredients, an azole derivative represented by general formula (I) above; and, as another one of the active ingredients, a compound having a β-tubulin synthesis inhibitory capacity.

A third aspect of an agricultural or horticultural chemical according to the present invention is an agricultural or horticultural chemical containing a plurality of active ingredients, the agricultural or horticultural chemical comprising: as one of the active ingredients, an azole derivative represented by general formula (I) above; and, as another one of the active ingredients, chlorothalonil.

A product for controlling plant diseases according to the present invention comprises: an azole derivative represented by general formula (I) above; and a compound having a succinate dehydrogenase inhibitory capacity, a compound having a β-tubulin synthesis inhibitory capacity, or chlorothalonil as a combination preparation for mixing and using a plurality of active ingredients.

A method of controlling plant diseases according to the present invention is a method comprising a step of performing foliage treatment or non-foliage treatment using the agricultural or horticultural chemical described above.

Advantageous Effects of Invention

Since the agricultural or horticultural chemical of the present invention contains a plurality of compounds as active ingredients, the agricultural or horticultural chemical can exhibit a synergistic effect and can demonstrate a strong controlling effect.

DESCRIPTION OF EMBODIMENTS

An embodiment of the agricultural or horticultural chemical, the product for controlling plant diseases, and the method of controlling plant diseases of the present invention will be described.

Agricultural or Horticultural Chemical

The agricultural or horticultural chemical of the present invention is a mixed formulation and contains a plurality of active ingredients. One of the active ingredients is an azole derivative represented by general formula (I) below. That is, the agricultural or horticultural chemical of the present invention contains at least one other compound as the active ingredient(s) in addition to the azole derivative represented by the general formula (I). In addition to an azole derivative represented by general formula (I) below as one active ingredient, an agricultural or horticultural chemical according to the present invention includes a compound having a succinate dehydrogenase inhibitory capacity, a compound having a β-tubulin synthesis inhibitory capacity, or chlorothalonil.

(1) Active Ingredients
(1-1) Azole Derivative

The agricultural or horticultural chemical according to the present invention contains, as one of the active ingredients, an azole derivative represented by general formula (I) below (hereinafter, referred to as azole derivative (I)).

[Formula 2]

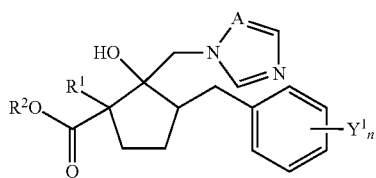

(I)

In general formula (I), $R^1$ is an alkyl group having from 1 to 6 carbons. Examples of the alkyl group having from 1 to 6 carbons include a methyl group, an ethyl group, a (1-methyl)ethyl group, an n-propyl group, a 1-methylpropyl group, a 2-methylpropyl group, an n-butyl group, a 1-methylbutyl group, a 2-methylbutyl group, a 1-ethylpropyl group, a 1,1-dimethylethyl group, an n-pentyl group, an n-hexyl group, and the like. Among these, an alkyl group having from 1 to 4 carbons is preferable as $R^1$, a methyl group and an ethyl group are more preferable, and a methyl group is still more preferable.

In general formula (I) above, $R^2$ represents a hydrogen atom, an alkyl group having from 1 to 3 carbons, an alkenyl group having from 2 to 3 carbons or an alkynyl group having from 2 to 3 carbons. Examples of the alkyl group having from 1 to 3 carbons include a methyl group, an ethyl group, a (1-methyl)ethyl group, an n-propyl group, and the like. Examples of the alkenyl group having from 2 to 3 carbons include a vinyl group, a 2-propenyl group, and the like. Examples of the alkynyl group having from 2 to 3 carbons include a 2-propynyl group, and the like. Of these, a hydrogen atom, a methyl group, an ethyl group and an n-propyl group are preferable as $R^2$, and a methyl group is more preferable.

In general formula (I), $Y^1$ represents a halogen atom. More specifically, examples of the halogen atom include a chlorine atom, a fluorine atom, a bromine atom, and an iodine atom. Of these, a chlorine atom and a fluorine atom are preferable as $Y^1$, and a chlorine atom is more preferable.

In general formula (I), n is either 0 or 1. In a case in which n is 1, it is not limited to the bonding position of $Y^1$, but a position that forms a 4-substituted benzyl group is preferred.

In general formula (I), A represents a nitrogen atom or a methine group. Among these, a nitrogen atom is preferable as A.

A preferred specific example of the azole derivative (I) is an azole derivative represented by general formula (Ia) below.

[Formula 3]

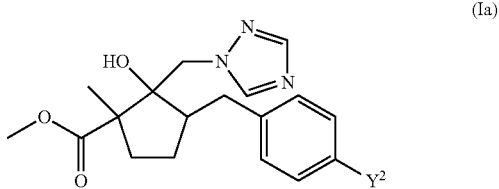

(Ia)

In this instance, in general formula (Ia), $Y^2$ represents a chlorine atom, a fluorine atom, or a hydrogen atom.

Additionally, in the azole derivative (I), there are stereoisomers based on the steric configuration of the organic groups that are bonded to the cyclopentane ring, and there are optical isomers of each stereoisomer. Accordingly, the azole derivative (I) may be either a substance that includes these isomers independently, or a substance that includes an arbitrary ratio of each isomer. Among the isomers, an azole derivative in which a hydroxy group that is bonded to the cyclopentane ring is a cis-type is preferable, and an azole derivative in which a hydroxy group and benzyl group that is either substituted with $R^1$ or unsubstituted that are bonded to the cyclopentane ring are a cis-types is more preferable.

In addition, the agricultural or horticultural chemical may include two or more types of azole derivative (I) in which at least one of $R^1$, $R^2$, A, $Y^1$, and n differs.

The azole derivative (I) exhibits excellent fungicidal activity against many types of fungi that cause plant diseases. Furthermore, the chemical containing the azole derivative (I) as an active ingredient has low toxicity toward human and animals and excellent safety in handling, and can exhibit a high controlling effect against a wide variety of plant diseases.

The method of producing the azole derivative (I) is not particularly limited, and the azole derivative (I) can be produced using a publicly known production method.

(1-2) Compound Having Succinate Dehydrogenase Inhibitory Capacity

In the first aspect of the agricultural or horticultural chemical according to the present invention, a compound having a succinate dehydrogenase inhibitory capacity (hereinafter, referred to as an SDHI compound) is included in addition to the azole derivative (I) as one active ingredient. An agricultural or horticultural chemical containing the SDHI compound and the azole derivative (I) as active ingredients can reduce the amount of dispersion of the chemicals required to obtain the same degree of effect as in a case in which the SDHI compound is used as a single agent.

Examples of the SDHI compound include bixafen, boscalid, penthiopyrad, fluxapyroxad, isopyrazam, benzovindiflupyr, fluopyram, furametpyr, thifluzamide, flutolanil, mepronil, fenfuram, carboxin, oxycarboxin, benzovindiflupyr, penflufen, sedaxane, isofetamide, mepronil, flutolanil, benodanil, and the like. Among these, bixafen, boscalid, fluxapyroxad, benzovindiflupyr, penthiopyrad and isopyrazam are particularly preferable. An agricultural or horticultural chemical that includes at least one of bixafen, boscalid, fluxapyroxad, benzovindiflupyr, penthiopyrad and isopyrazam exhibits particularly high activity. A single type of SDHI compound may be included in the agricultural or horticultural chemical, or a plurality of types of SDHI compound may be included therein.

Bixafen, boscalid, fluxapyroxad, benzovindiflupyr, penthiopyrad, isopyrazam and other SDHI compounds can be obtained from commercially available formulations or can be produced using a publicly known production method.

(1-3) Compound having β-tubulin Synthesis Inhibitory Capacity

In the second aspect of the agricultural or horticultural chemical according to the present invention, a compound having a β-tubulin synthesis inhibitory capacity is included in addition to the azole derivative (I) as one active ingredient. The agricultural or horticultural chemical containing the compound having a β-tubulin synthesis inhibitory capacity and the azole derivative (I) as active ingredients can reduce the amount of dispersion of the chemicals required to obtain the same degree of effect as in a case in which the compound having a β-tubulin synthesis inhibitory capacity is used as a single agent.

Examples of the compound having a β-tubulin synthesis inhibitory capacity include benomyl, carbendazim, fuberidazole, thiabendazole, thiophanate, thiophanate-methyl, zoxamide, ethaboxam, diethofencarb, and the like. Among these, thiophanate-methyl is preferable. An agricultural or horticultural chemical that includes thiophanate-methyl exhibits particularly high activity. A single type of compound having a β-tubulin synthesis inhibitory capacity may be included in the agricultural or horticultural chemical, or a plurality of types of compound having a β-tubulin synthesis inhibitory capacity may be included therein. Thiophanate-methyl and other compounds having a β-tubulin synthesis inhibitory capacity can be obtained from commercially available formulations or can be produced using a publicly known production method.

(1-4) Chlorothalonil

In the third aspect of the agricultural or horticultural chemical according to the present invention, chlorothalonil is included in addition to the azole derivative (I) as one active ingredient. The agricultural or horticultural chemical containing chlorothalonil and the azole derivative (I) as active ingredients can reduce the amount of dispersion of the chemicals required to obtain the same degree of effect as in a case in which chlorothalonil is used as a single agent. Chlorothalonil can be obtained from commercially available formulations or can be produced using a publicly known production method.

(2) Formulation

In an embodiment of the agricultural or horticultural chemical according to the present invention, the mixing ratio of the azole derivative (I) to active ingredients other than the azole derivative (I) (the total amount thereof in cases in which a plurality of compounds are included) is, in terms of weight ratio, preferably from 1000:1 to 1:1000, more preferably from 750:1 to 1:750, and still more preferably from 500:1 to 1:500. Additionally, in cases in which a plurality of active ingredients are included as the active ingredients other than the azole derivative (I), the mixing ratio of the active ingredients other than the azole derivative (I) can be set as appropriate depending on the uses of the chemicals.

The agricultural or horticultural chemical may contain solid carriers, liquid carriers (diluents), surfactants, or other formulation aids, in addition to the active ingredients described above. Thus, the form of the agricultural or horticultural chemical may take on various forms such as a powder, a wettable powder, granules, or an emulsion.

In the agricultural or horticultural chemical, the total content of the azole derivative (I) and active ingredients other than the azole derivative (I) is preferably from 0.1 to 95% by weight, more preferably from 0.5 to 90% by weight, and still more preferably from 2 to 80% by weight, relative to the total amount of the agricultural or horticultural chemical.

Examples of solid carriers that are used as formulation aids include talc, kaolin, bentonite, diatomaceous earth, white carbon, clay, and the like. Examples of liquid carriers that are used as formulation aids include water, xylene, toluene, chlorobenzene, cyclohexane, cyclohexanone, dimethylsulfoxide, dimethylformamide, alcohol, and the like. Surfactants that are used as formulation aids may be used for different purposes depending on their effect. For example, in the case of an emulsifier, polyoxyethylene alkyl aryl ether, polyoxyethylene sorbitan monolaurate, and the like may be used. In the case of a dispersant, lignin sulfonate, dibutyl napthalene sulfonate, and the like may be used. In the case of a wetting agent, alkyl sulfonate, alkyl phenyl sulfonate, and the like may be used.

The agricultural or horticultural chemical may be used in an unmodified state, or may be used after dilution to a predetermined concentration using a diluent such as water. When used after being diluted, the total concentration of the active ingredients is preferably within the range of from 0.001 to 1.0% relative to the total amount of the chemical agent after dilution.

Since the agricultural or horticultural chemical according to the present invention exhibits a synergistic effect in its controlling effect of plant diseases, the agricultural or horticultural chemical can reduce the used amount of the compounds required to obtain the same degree of effect as in a case in which the azole derivative (I) or another active ingredient that is included with the azole derivative (I), is used as a single agent. For this reason, toxicity in non-target organisms and environmental load can be reduced. In addition, it is anticipated that the emergence of chemical-resistant fungi can be suppressed because the used amount of the respective compounds can be reduced. Furthermore, since the agricultural or horticultural chemical of the present invention contains two ingredients having significantly different molecular structures as the active ingredients for the plant disease controlling effect, the agricultural or horticultural chemical offers a broad spectrum of disease control.

The agricultural or horticultural chemical may be prepared by formulating each of the active ingredients separately and then mixing them to produce a formulated agricultural or horticultural chemical. Therefore, a product for controlling plant diseases that contains the azole derivative (I) and the other active ingredient separately, as preparations for blending by which ingredients are mixed for use in controlling plant diseases, is also included in the scope of the present invention. In cases in which two or more active ingredients other than the azole derivative (I) are included, the active ingredients other than the azole derivative (I) may also be separate.

(3) Plant Disease Controlling Effect

The agricultural or horticultural chemical of the present invention exhibits a controlling effect against a wide range of plant diseases. Examples of applicable diseases include the following. Note that, in the parenthesis after each disease name, major pathogenic fungus (fungi) that causes the disease is(are) indicated.

That is, applicable diseases include soybean rust (*Phakopsora pachyrhizi, Phakopsora meibomiae*), soybean septoria brown spot (*Septoria glycines*), soybean purpura (*Cercospora kikuchii*), rice blast (*Pyricularia grisea*), rice sesame leaf blight (*Cochliobolus miyabeanus*), rice bacterial leaf blight (*Xanthomonas oryzae*), rice sheath blight (*Rhizoctonia solani*), rice stem rot (*Helminthosporium sig-* moideun), rice bakanae disease (*Gibberella fujikuroi*), rice seedling blight (*Pythium aphanidermatum*), barley powdery mildew (*Erysiphe graminis f. Sp hordei*), barley stem rust (*Puccinia graminis*), barley yellow rust (*Puccinia striiformis*), barley mottle-leaf (*Pyrenophora graminea*), barley scald (*Rhynchosporium secalis*), barley loose kernel smut (*Ustilago nuda*), barley net blotch (*Pyrenophora teres*), barley Fusarium head blight (*Fusarium graminearum, Microdochium nivale*), wheat powdery mildew (*Erysiphe graminis f. Sp tritici*), wheat leaf rust (*Puccinia recondita*), wheat yellow rust (*Puccinia striiformis*), wheat eyespot disease (*Pseudocercosporella herpotrichoides*), wheat Fusarium head blight (*Fusarium graminearum, Microdochium nivale*), wheat glume blotch (*Phaeosphaeria nodorum*), wheat leaf blight (*Septoria tritici*), wheat pink snow mold (*Microdochium nivale*), wheat damping off (*Gaeumannomyces graminis*), wheat black spot disease (*Epicoccum spp*), wheat macular disease (*Pyrenophora tritici-repentis*), corn smut (*Ustilago maydis*), corn anthracnose (*Colletotrichum graminicola*), corn brown spot disease (*Kabatiella zeae*), corn gray leaf spot (*Cercospora zeae-maydis*), northern leaf blight (*Setosphaeria turcica*), corn northern leaf spot (*Cochliobolus carbonum*), corn leaf spot (*Physoderma maydis*), corn rust (*Puccinia* spp), corn sesame leaf blight (*Bipolaris maydis*), corn yellow sesame leaf blight (*Phyllosticta maydis*), corn Fusarium head blight (*Gibberella zeae*), sugarcane rust (*Puccinia* spp), Cucurbitaceae powdery mildew (*Sphaerotheca fuliginea*), anthracnose (*Colletotrichum lagenarium, Glomerella cingulata*), cucumber downy mildew (*Pseudoperonospora cubensis*), cucumber gray plague (*Phytophthora capsici*), cucumber vine wilt (*Fusarium oxysporum f.sp.cucumerinum*), watermelon vine wilt (*Fusarium oxysporum f.sp.niveum*), apple powdery mildew (*Podosphaera leucotricha*), apple scab (*Venturia inaequalis*), apple monilia disease (*Monilinia mali*), apple leaf spot disease (*Alternaria alternata*), apple franc disease (*Valsa mali*), pear black spot disease (*Alternaria kikuchiana*), pear powdery mildew (*Phyllactinia pyri*), pear chocolate spot (*Gymnosporangium asiaticum*), pear scab (*Venturia nashicola*), strawberry powdery mildew (*Sphaerotheca humuli*), stone fruit orchard brown rot (*Monilinia fructicola*), citrus blue mold (*Penicillium italicum*), grape powdery mildew (*Uncinula necator*), grape downy mildew (*Plasmopara viticola*), grape evening rot (*Glomerella cingulata*), grape rust (*Phakopsora ampelopsidis*), tomato powdery mildew (*Erysiphe cichoracearum*), tomato early blight (*Alternaria solani*), eggplant powdery mildew (*Erysiphe cichoracearum*), potato early blight (*Alternaria solani*), tobacco powdery mildew (*Erysiphe cichoracearum*), tobacco chocolate spot (*Alternaria longipes*), sugar beet brown spot *Cercospora beticola* (*Cercospora beticola*), radish chlorosis (*Fusarium oxysporum f.sp.raphani*), gray mold disease that affects a variety of crops (*Botrytis cinerea*) and rot (*Sclerotinia sclerotiorum*), and the like.

In addition, examples of applicable plants include wild plants, cultivars, plants and cultivars bred by conventional hybridizing or plasmogamy, and genetically recombinant plants and cultivars obtained by gene manipulation. Examples of genetically recombined plants and cultivars include herbicide-tolerant crops, pest-resistant crops in which an insecticidal protein-producing gene has been recombined, pathogen-resistant crops in which a pathogen resistance derivative-producing gene has been recombined, taste-improved crops, yield-improved crops, preservation-improved crops, yield-improved crops, and the like. Specific examples of genetically recombined cultivars include the brand names Roundup Ready, Liberty Link, Clearfield, Yieldgard, Herculex, Bollgard, and the like.

In addition, an embodiment of the agricultural or horticultural chemical of the present invention exhibits an effect of increasing the amount of harvest by regulating the growth or an effect of enhancing the quality of a wide variety of crops and garden plants. Examples of these crops include wheats such as wheat, barley, and oat, food crops such as rice, rapeseed, sugar cane, corn, maize, soy bean, pea, peanut, and sugar beet, cabbage, garlic, radish, carrot, apple, pear, citruses such as mandarin orange, orange and lemon, peach, cherry, avocado, mango, papaya, red pepper, cucumber, melon, strawberry, tobacco, tomato, eggplant, lawn, chrysanthemum, azalea, and other decorative plants.

Furthermore, the azole derivative (I) exhibits an excellent effect in protecting materials from a wide variety of harmful microorganisms that erode industrial materials, and can be used as an active ingredient for industrial material protectants. Because of this, an embodiment of the agricultural or horticultural chemical of the present invention can be also used as an industrial material protectant.

(4) Other Active Ingredients

The agricultural or horticultural chemical of the present invention can be used in combination with other known active ingredients (active ingredients contained in fungicides, insecticides, miticides, or herbicides, and plant growth regulating agents) in addition to the active ingredients described above in order to enhance the performance as an agricultural or horticultural chemical.

Plant Disease Controlling Method

The agricultural or horticultural chemical of the present invention can be used not only in foliage treatment such as foliage spraying but also in non-foliage treatment such as seed treatment, soil-drenching treatment, or water surface treatment. Therefore, the method of controlling plant diseases of the present invention comprises a step of performing foliage treatment or non-foliage treatment using the agricultural or horticultural chemical described above. When non-foliage treatment is performed, the amount of labor required can be reduced in comparison to when foliage treatment is performed.

In the case of application by seed treatment, the chemical is deposited on seeds by mixing and stirring a wettable powder and a powder and the like with seeds or immersing seeds in a diluted wettable powder or the like. The total amount of active ingredients used in the case of seed treatment is, for example, from 0.01 to 10,000 g and preferably from 0.1 to 1,000 g per 100 kg of seeds. Seeds that have been treated with the agricultural or horticultural chemical may be used in the same manner as ordinary seeds.

In the case of application by irrigation treatment, a planting hole or the vicinity thereof may be treated with granules or the like at the time of the transplantation of seedling or the like, or seeds or the earth around a plant may be treated with granules, a wettable powder, or the like. The total amount of active ingredients used in the case of irrigation treatment is, for example, from 0.01 to 10,000 g and preferably from 0.1 to 1,000 g per 1 $m^2$ of agricultural or horticultural area.

In the case of application by water surface treatment, the water surface of a paddy field may be treated with granules or the like. The total amount of active ingredients used in the case of water surface treatment is, for example, from 0.1 to 10,000 g and preferably from 1 to 1,000 g per 10 a of the paddy field.

The total amount of active ingredients used for foliar spraying is, for example, from 20 to 5,000 g and preferably from 50 to 2,000 g per 1 ha of the agricultural or horticultural area such as a field, a rice paddy, an orchard, or a greenhouse.

Additionally, since the concentration and quantity used differ depending on the form of the agent, time of use, usage method, usage location, target crops and the like, they may be increased or decreased within the above ranges.

SUMMARY

In the abovementioned manner, the first aspect of an agricultural or horticultural chemical according to the present invention is an agricultural or horticultural chemical containing a plurality of active ingredients, the agricultural or horticultural chemical comprising: as one of the active ingredients, an azole derivative represented by general formula (I) below; and, as another one of the active ingredients, a compound having a succinate dehydrogenase inhibitory capacity.

[Formula 4]

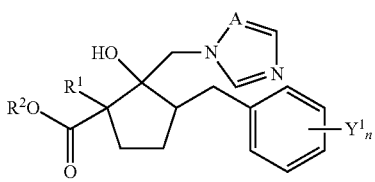

(I)

Additionally, in general formula (I), $R^1$ represents an alkyl group having from 1 to 6 carbons, $R^2$ represents a hydrogen atom, an alkyl group having from 1 to 3 carbons, an alkenyl group having from 2 to 3 carbons or an alkynyl group having from 2 to 3 carbons, A represents a nitrogen atom or a methine group, $Y^1$ represents a halogen atom, and n represents either 0 or 1.

In addition, in the first aspect of an agricultural or horticultural chemical according to the present invention, it is preferable that the above-mentioned compound having a succinate dehydrogenase inhibitory capacity be at least one of bixafen, boscalid, fluxapyroxad, penthiopyrad, benzovindiflupyr, and isopyrazam.

In addition, a second aspect of an agricultural or horticultural chemical according to the present invention is an agricultural or horticultural chemical containing a plurality of active ingredients, the agricultural or horticultural chemical comprising: as one of the active ingredients, an azole derivative represented by general formula (I) above; and, as another one of the active ingredients, a compound having a β-tubulin synthesis inhibitory capacity.

In addition, in the second aspect of the agricultural or horticultural chemical according to the present invention, it is preferable that the compound having a β-tubulin synthesis inhibitory capacity be thiophanate-methyl.

In addition, a third aspect of an agricultural or horticultural chemical according to the present invention is an agricultural or horticultural chemical containing a plurality of active ingredients, the agricultural or horticultural chemical comprising: as one of the active ingredients, an azole derivative represented by general formula (I) above; and, as another one of the active ingredients, chlorothalonil.

Furthermore, the agricultural or horticultural chemical of the present invention is preferably used as a fungicide.

In addition, in the agricultural or horticultural chemical according to the present invention, it is preferable that the above-mentioned azole derivative be an azole derivative represented by general formula (Ia) below.

[Formula 5]

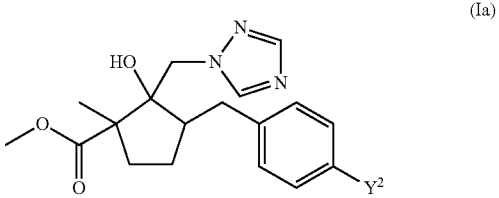

(Ia)

Additionally, in general formula (Ia), $Y^2$ represents a chlorine atom, a fluorine atom or a hydrogen atom.

A product for controlling plant diseases according to the present invention separately comprises: an azole derivative represented by general formula (I) above; and a compound having a succinate dehydrogenase inhibitory capacity, a compound having a β-tubulin synthesis inhibitory capacity, or chlorothalonil as a combination preparation for mixing and using a plurality of active ingredients.

A method of controlling plant diseases according to the present invention is a method comprising a step of performing foliage treatment or non-foliage treatment using the agricultural or horticultural chemical described above.

Embodiments of the present invention will be described in further detail hereinafter using working examples. Of course, the present invention is not limited to the examples below, and it goes without saying that various modes are possible with regard to the details thereof. Furthermore, the present invention is not limited to the embodiments described above, and various modifications are possible within the scope indicated in the claims. Embodiments obtained by appropriately combining the technical means disclosed by the embodiments are also included in the technical scope of the present invention. In addition, all of the documents disclosed in the present specification are hereby incorporated by reference.

EXAMPLES

Antimicrobial properties were tested for a mixed formulation of 3-(4-chlorobenzyl)-2-hydroxy-1-methyl-2-(1H-1,2,4-triazol-1-ylmethyl) cyclopentane carboxylic acid methyl (hereinafter, referred to as compound (1)) and other compounds.

Test Example 1

In vitro Antimicrobial Activity Test Using Compound (1) and bixafen

In the present test example, the antimicrobial properties of a mixed formulation of compound (1) and bixafen on wheat leaf blight (*Septoria tritici*) were tested.

Agar plates containing chemical(s) were produced by mixing, into a potato dextrose agar culture medium (a PDA culture medium), compound (1) only, bixafen only, or compound (1) and bixafen in a manner in which the mixture attained a predetermined concentration. Meanwhile, wheat leaf blight was punched out from the periphery of a colony of wheat leaf blight that was cultured in advance on an agar plates that did not include the chemicals, using a cork borer having a diameter of 4 mm, and inoculated onto the PDA agar plates in which the chemical(s) was(were) mixed. After culturing at 20° C. for three days, the diameter of the grown colonies were measured, and a fungal growth inhibition rate was determined by comparing the diameter with the diameter of a colony on the culture medium that did not include the chemicals using the following formula.

$$R=100\,(dc-dt)/dc$$

Additionally, in the above formula, R represents a fungal expansion suppression rate (%), dc represents the diameter of a colony on an untreated plate, and dt represents the diameter of a colony on an chemical-treated plate. Next, determination if the synergistic effect of the two types of compounds was carried out using a method that used Colby's formula (the following formula).

Inhibition rate during mixed use (theoretical value)=$\alpha$+ $((100-\alpha)\times\beta)/100$, note that, in the formula above, $\alpha$ and $\beta$ respectively represent the inhibition rates of the compounds during single use of the compounds.

The results are shown in Table 1. The fact that the growth inhibition rate when the compound (1) and the bixafen were mixed was greater than the theoretical values calculated from the inhibition rates in cases of single use of the respective compounds made it clear that the compound (1) and the bixafen exhibited a synergistic effect.

TABLE 1

| Compound (1) | Bixafen | Fungal growth inhibition rate (%) | |
|---|---|---|---|
| ppm | ppm | Measured value | Theoretical value |
| 0 | 2.5 | 54 | — |
| 0 | 0.63 | 31 | — |
| 0 | 0.1575 | 6 | — |
| 0 | 0.0393 | 0 | — |
| 0.005 | 0 | 0 | — |
| 0.005 | 2.5 | 76 | 54 |
| 0.005 | 0.63 | 41 | 31 |
| 0.005 | 0.1575 | 14 | 6 |
| 0.005 | 0.0393 | 0 | 0 |

Test Example 2

In vitro Antimicrobial Activity Test Using Compound (1) and bixafen

In the present test example, the antimicrobial properties of a mixed formulation of compound (1) and bixafen on wheat damping off (*Gaeumannomyces graminis*) were tested.

Agar plates containing chemical(s) were produced by mixing, into a PDA culture medium, compound (1) only, bixafen only, or compound (1) and bixafen in a manner in which the mixture attained a predetermined concentration. Meanwhile, wheat damping off was punched out from the periphery of a colony of wheat damping off using a cork borer having a diameter of 4 mm, and inoculated onto the PDA agar plates in which the chemical(s) was(were) mixed. After culturing at 20° C. for three days, the diameter of the grown colonies were measured, and the fungal growth inhibition rate was determined by comparing the diameter with the diameter of a colony on the culture medium that did not include the chemicals in the same manner as Test Example 1. In addition, the determination of the synergistic effect was carried out using a method that used Colby's formula in the same manner as Test Example 1.

The results are shown in Table 2. The fact that the growth inhibition rate when the compound (1) and the bixafen were mixed was greater than the theoretical values calculated from the inhibition rates in cases of single use of the respective compounds made it clear that the compound (1) and the bixafen exhibited a synergistic effect.

TABLE 2

| Compound (1) | Bixafen | Fungal growth inhibition rate (%) | |
|---|---|---|---|
| ppm | ppm | Measured value | Theoretical value |
| 0 | 2.5 | 29 | — |
| 0 | 0.63 | 4 | — |
| 0 | 0.1575 | 3 | — |
| 0 | 0.0393 | 0 | — |
| 0.005 | 0 | 0 | — |
| 0.005 | 2.5 | 40 | 29 |
| 0.005 | 0.63 | 18 | 4 |
| 0.005 | 0.1575 | 18 | 3 |
| 0.005 | 0.0393 | 7 | 0 |

Test Example 3

In vitro Antimicrobial Activity Test Using Compound (1) and isopyrazam

In the present test example, the antimicrobial properties of a mixed formulation of compound (1) and isopyrazam on gray mold disease (Botrytis cinerea) were tested.

Agar plates containing chemical(s) were produced by mixing, into a PDA culture medium, compound (1) only, isopyrazam only, or compound (1) and isopyrazam in a manner in which the mixture attained a predetermined concentration. Meanwhile, gray mold disease was punched out from the periphery of a colony of gray mold disease that was cultured in advance on an agar plates that did not include the chemicals, using a cork borer having a diameter of 4 mm, and inoculated onto the PDA agar plates in which the chemical(s) was(were) mixed. After culturing at 20° C. for two days, the diameter of the grown colonies were measured, and the fungal growth inhibition rate was determined by comparing the diameter with the diameter of a colony on the culture medium that did not include the chemicals in the same manner as Test Example 1. In addition, the determination of the synergistic effect was carried out using a method that used Colby's formula in the same manner as Test Example 1.

The results are shown in Table 3. The fact that the growth inhibition rate when the compound (1) and the isopyrazam were mixed was greater than the theoretical values calculated from the inhibition rates in cases of single use of the respective compounds made it clear that the compound (1) and the isopyrazam exhibited a synergistic effect.

TABLE 3

| Compound (1) | Isopyrazam | Fungal growth inhibition rate (%) | |
|---|---|---|---|
| ppm | ppm | Measured value | Theoretical value |
| 0 | 10 | 69 | — |
| 0 | 2.5 | 35 | — |
| 0 | 0.63 | 23 | — |
| 0 | 0.1575 | 9 | — |
| 0 | 0.0393 | 1 | — |
| 0.078 | 0 | 4 | — |
| 0.078 | 10 | 72 | 70 |
| 0.078 | 2.5 | 57 | 38 |

TABLE 3-continued

| Compound (1) | Isopyrazam | Fungal growth inhibition rate (%) | |
|---|---|---|---|
| ppm | ppm | Measured value | Theoretical value |
| 0.078 | 0.63 | 47 | 26 |
| 0.078 | 0.1575 | 40 | 13 |
| 0.078 | 0.0393 | 23 | 6 |

Test Example 4

In vitro Antimicrobial Activity Test Using Compound (1) and boscalid

In the present test example, the antimicrobial properties of a mixed formulation of compound (1) and boscalid on wheat leaf blight (*Septoria tritici*) were tested.

Agar plates containing chemical(s) were produced by mixing, into a PDA culture medium, compound (1) only, boscalid only, or compound (1) and boscalid in a manner in which the mixture attained a predetermined concentration. Meanwhile, wheat leaf blight was punched out from the periphery of a colony of wheat leaf blight that was cultured in advance on an agar plates that did not include the chemicals, using a cork borer having a diameter of 4 mm, and inoculated onto the PDA agar plates in which the chemical(s) was(were) mixed. After culturing at 25° C. for 14 days, the diameter of the grown colonies were measured, and the fungal growth inhibition rate was determined by comparing the diameter with the diameter of a colony on the culture medium that did not include the chemicals in the same manner as Test Example 1. In addition, the determination of the synergistic effect was carried out using a method that used Colby's formula in the same manner as Test Example 1.

The results are shown in Table 4. The fact that the growth inhibition rate when the compound (1) and the boscalid were mixed was greater than the theoretical values calculated from the inhibition rates in cases of single use of the respective compounds made it clear that the compound (1) and the boscalid exhibited a synergistic effect.

TABLE 4

| Compound (1) | Boscalid | Fungal growth inhibition rate (%) | |
|---|---|---|---|
| ppm | ppm | Measured value | Theoretical value |
| 0 | 10 | 100 | — |
| 0 | 2.5 | 49 | — |
| 0 | 0.63 | 31 | — |
| 0 | 0.1575 | 0 | — |
| 0 | 0.0393 | 0 | — |
| 0.02 | 0 | 0 | — |
| 0.02 | 10 | 100 | 100 |
| 0.02 | 2.5 | 62 | 49 |
| 0.02 | 0.63 | 35 | 31 |
| 0.02 | 0.1575 | 6 | 0 |
| 0.02 | 0.0393 | 6 | 0 |

Test Example 5

In vitro Antimicrobial Activity Test Using Compound (1) and thiophanate-methyl

In the present test example, the antimicrobial properties of a mixed formulation of compound (1) and thiophanate-methyl on wheat leaf blight (*Septoria tritici*) were tested.

Testing and determination were performed in the same manner as in Test Example 4 except for using the thiophanate-methyl in place of the boscalid.

The results are shown in Table 5. The fact that the growth inhibition rate when the compound (1) and the thiophanate-methyl were mixed was greater than the theoretical values calculated from the inhibition rates in cases of single use of the respective compounds made it clear that the compound (1) and the thiophanate-methyl exhibited a synergistic effect.

TABLE 5

| Compound (1) | Thiophanate-methyl | Fungal growth inhibition rate (%) | |
|---|---|---|---|
| ppm | ppm | Measured value | Theoretical value |
| 0 | 2.5 | 100 | — |
| 0 | 0.625 | 76 | — |
| 0 | 0.156 | 0 | — |
| 0 | 0.039 | 0 | — |
| 0 | 0.010 | 0 | — |
| 0.005 | 0 | 23 | — |
| 0.005 | 2.5 | 100 | 100 |
| 0.005 | 0.625 | 100 | 81 |
| 0.005 | 0.156 | 30 | 23 |
| 0.005 | 0.039 | 33 | 23 |
| 0.005 | 0.010 | 28 | 23 |

Test Example 6

In vitro Antimicrobial Activity Test Using Compound (1) and chlorothalonil

In the present test example, the antimicrobial properties of a mixed formulation of compound (1) and chlorothalonil on wheat leaf blight (Septoria tritici) were tested.

Test and determination were performed in the same manner as in Test Example 4 except for using the chlorothalonil in place of the boscalid.

The results are shown in Table 6. The fact that the growth inhibition rate when the compound (1) and the chlorothalonil were mixed was greater than the theoretical values calculated from the inhibition rates in cases of single use of the respective compounds made it clear that the compound (1) and the chlorothalonil exhibited a synergistic effect.

TABLE 6

| Compound (1) | Chlorothalonil | Fungal growth inhibition rate (%) | |
|---|---|---|---|
| ppm | ppm | Measured value | Theoretical value |
| 0 | 2.5 | 30 | — |
| 0 | 0.625 | 3 | — |
| 0 | 0.156 | 0 | — |
| 0 | 0.039 | 0 | — |
| 0 | 0.010 | 0 | — |
| 0.005 | 0 | 81 | — |
| 0.005 | 2.5 | 100 | 86 |
| 0.005 | 0.625 | 84 | 81 |
| 0.005 | 0.156 | 83 | 81 |
| 0.005 | 0.039 | 85 | 81 |
| 0.005 | 0.010 | 87 | 81 |

Test Example 7

In vitro Antimicrobial Activity Test Using Compound (1) and fluxapyroxad

In the present test example, the antimicrobial properties of a mixed formulation of compound (1) and fluxapyroxad on wheat leaf blight (*Septoria tritici*) were tested.

Test and determination were performed in the same manner as in Test Example 4 except for using the fluxapyroxad in place of the boscalid.

The results are shown in Table 7. The fact that the growth inhibition rate when the compound (1) and the fluxapyroxad were mixed was greater than the theoretical values calculated from the inhibition rates in cases of single use of the respective compounds made it clear that the compound (1) and the fluxapyroxad exhibited a synergistic effect.

TABLE 7

| Compound (1) | Fluxapyroxad | Fungal growth inhibition rate (%) | |
|---|---|---|---|
| ppm | ppm | Measured value | Theoretical value |
| 0 | 10.00 | 100 | — |
| 0 | 2.50 | 100 | — |
| 0 | 0.63 | 74 | — |
| 0 | 0.16 | 34 | — |
| 0 | 0.04 | 11 | — |
| 0.02 | 0 | 7 | — |
| 0.02 | 10.00 | 100 | 100 |
| 0.02 | 2.50 | 100 | 100 |
| 0.02 | 0.63 | 98 | 76 |
| 0.02 | 0.16 | 61 | 38 |
| 0.02 | 0.04 | 30 | 17 |

Test Example 8

In vitro Antimicrobial Activity Test Using Compound (1) and penthiopyrad

In the present test example, the antimicrobial properties of a mixed formulation of compound (1) and penthiopyrad on gray mold disease (*Botrytis cinerea*) were tested.

Test and determination were performed in the same manner as in Test Example 3 except for using the penthiopyrad in place of the isopyrazam.

The results are shown in Table 8. The fact that the growth inhibition rate when the compound (1) and the penthiopyrad were mixed was greater than the theoretical values calculated from the inhibition rates in cases of single use of the respective compounds made it clear that the compound (1) and the penthiopyrad exhibited a synergistic effect.

TABLE 8

| Compound (1) | Penthiopyrad | Fungal growth inhibition rate (%) | |
|---|---|---|---|
| ppm | ppm | Measured value | Theoretical value |
| 0 | 10.00 | 93 | — |
| 0 | 2.50 | 61 | — |
| 0 | 0.63 | 31 | — |
| 0.078 | 0 | 13 | — |
| 0.078 | 10.00 | 98 | 94 |
| 0.078 | 2.50 | 90 | 66 |
| 0.078 | 0.63 | 60 | 40 |

INDUSTRIAL APPLICABILITY

The present invention can be suitably used as an active ingredient of controlling agents that can control plant diseases while minimizing harmful effects to the plants.

The invention claimed is:

1. An agricultural or horticultural chemical containing a plurality of active ingredients, the agricultural or horticultural chemical comprising:
   as one of active ingredients, an azole derivative represented by general formula (I) below; and,
   as another one of the active ingredients, a compound having a succinate dehydrogenase inhibitory capacity,

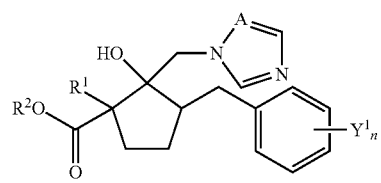

(I)

wherein, in general formula (I), $R^1$ represents an alkyl group having from 1 to 6 carbons, $R^2$ represents a hydrogen atom, an alkyl group having from 1 to 3 carbons, an alkenyl group having from 2 to 3 carbons or an alkynyl group having from 2 to 3 carbons, A represents a nitrogen atom or a methine group, $Y^1$ represents a halogen atom, and n represents either 0 or 1.

2. The agricultural or horticultural chemical according to claim 1, wherein the compound having a succinate dehydrogenase inhibitory capacity is at least one of bixafen, boscalid, fluxapyroxad, penthiopyrad, benzovindiflupyr, and isopyrazam.

3. The agricultural or horticultural chemical according to claim 1, wherein the agricultural or horticultural chemical is a fungicide.

4. The agricultural or horticultural chemical according to claim 1, wherein the azole derivative is an azole derivative represented by general formula (Ia),

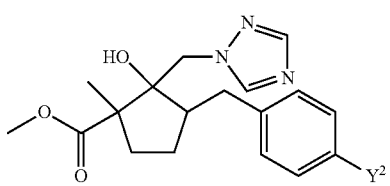

(Ia)

wherein, in general formula (Ia), $Y^2$ is a chlorine atom, a fluorine atom or a hydrogen atom).

* * * * *